(12) United States Patent  
Lenhardt et al.

(10) Patent No.: US 8,172,769 B2
(45) Date of Patent: May 8, 2012

(54) METHOD AND APPARATUS FOR MONITORING INTRA OCULAR AND INTRA CRANIAL PRESSURE

(75) Inventors: Martin M Lenhardt, Hayes, VA (US); Kevin Ward, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 279 days.

(21) Appl. No.: 10/565,852

(22) PCT Filed: Aug. 6, 2004

(86) PCT No.: PCT/US2004/025185
§ 371 (c)(1),
(2), (4) Date: Nov. 30, 2006

(87) PCT Pub. No.: WO2005/016121
PCT Pub. Date: Feb. 24, 2005

(65) Prior Publication Data
US 2007/0123796 A1  May 31, 2007

(51) Int. Cl.
*A61B 5/00* (2006.01)
(52) U.S. Cl. ...................................... 600/561
(58) Field of Classification Search .................. 600/561, 600/587, 398, 399, 400, 402, 405, 406
See application file for complete search history.

(56) References Cited

U.S. PATENT DOCUMENTS

| | | | |
|---|---|---|---|
| 3,903,871 A * | 9/1975 | Chisum et al. | 600/489 |
| 5,117,835 A | 6/1992 | Mick | |
| 5,129,403 A * | 7/1992 | Henriquez et al. | 600/586 |
| 5,840,041 A | 11/1998 | Petter et al. | |
| 5,919,144 A * | 7/1999 | Bridger et al. | 600/561 |
| 5,951,477 A * | 9/1999 | Ragauskas et al. | 600/438 |
| 6,423,001 B1 * | 7/2002 | Abreu | 600/405 |
| 6,749,568 B2 | 6/2004 | Fleischman et al. | |
| 2003/0191411 A1 * | 10/2003 | Yost et al. | 600/561 |

* cited by examiner

*Primary Examiner* — Max Hindenburg
*Assistant Examiner* — Fangemonique Smith
(74) *Attorney, Agent, or Firm* — Whitham Curtis Christofferosn & Cook, PC

(57) ABSTRACT

A method and apparatus for measuring acoustic energy applied to the head to detect increases in intracranial pressure. Acoustic eye patches are applied to a patient's eye or eyelid, and an ultrasonic sweep generator applies an acoustic signal across the patient's skull, the signal being swept across a predetermined range. The eye patches have piezoelectric film sensors for measuring the acoustic signal. In one embodiment the predetermined range is in the ultrasonic band and an analyzer determines from the output of the sensors a resonant frequency and a damping of acoustic amplitude at said resonant frequency, there being a correlation between said damping and intra cranial pressure. In another embodiment the predetermined range includes a range less than 20 kHz and the analyzer determines retinal artery pulsations, with pressure being applied to the eye until the pulsations disappear, such pressure being a measure of intra cranial pressure.

14 Claims, 10 Drawing Sheets resonance estimated modeling eye globe as a sphere acoustically coupled to the brain $F_0 \sim 33 - 43$ kHz increased damping piezoelectric film sensor placed in contact with eye or eyelid Direct ICP measurement (calibration)

| Patient 510 | Invasive Method Monitoring 520 | ICP 530 |
|---|---|---|
| HB | Ventriculostomy | 7 mm Hg. |
| GC | Ventriculostomy | 11 mm Hg. |
| GJ | Ventriculostomy | 15 mm Hg. |
| RR | Ventriculostomy | 20 mm Hg. |
| BP | Ventriculostomy | 18 mm Hg. |

*Figure 5*

ICP values between patients (N = 5)

| ICPΔ | ΔdBV |
|---|---|
| 11 - 7 | -4.7* |
| 11 - 15 | 10.3* |
| 11 - 18 | 13* |
| 11 - 20 Hg | 12.9* |

| ICPΔ | ΔdBV |
|---|---|
| 7 - 11 | -4.7* |
| 7 - 15 | 9.2* |
| 7 - 20 | 11.3* |

* significant at the $p = 0.0001$ level

*Figure 10*

METHOD AND APPARATUS FOR MONITORING INTRA OCULAR AND INTRA CRANIAL PRESSURE

BACKGROUND OF THE INVENTION

1. Field of the Invention

The present invention generally relates to non-invasive techniques for diagnosis of medical conditions, and in particular to use of such techniques for monitoring pressure within the cranium.

2. Background Description

Pressure increase in the brain, which is contained within the skull, is a serious medical condition that can be life threatening. The brain is surrounded by cerebrospinal fluid; the pressure of the fluid, known as intra cranial pressure (ICP), is carefully controlled by homeostatic mechanisms in the body. In pathological circumstances such as stroke or head injury, elevated ICP poses a clinical problem that must be carefully managed to prevent severe brain damage or even the death of the patient. Intra cranial pressure changes can be detected non invasively using acoustic stimulation and analysis. The brain and the skull are coupled resonant systems that will respond in a predictable fashion to pressure increases given the bioboundary conditions. Changes in acoustic damping are correlated with changes in cerebral spinal fluid (CSF) or intra cranial pressure (ICP). Intra cranial pressure is currently monitored invasively, with monitoring devices implanted within the skull cavity or lumbar punctures.

There are two "windows" to the interior of the skull for "seeing" brain pressure: the ear and the eye. Intra cranial pressure (ICP) in the brain is DIRECTLY communicated to both the eye and ear. The eye is more convenient to non invasively monitor changes in ICP. Ear monitoring of changes in cerebral spinal fluid (CSF) pressure have been attempted but have not resulted in a feasible clinical device. Direct measures of skull vibration by using ultrasonic probes have also been attempted, but with limited success because it is technically complicated, and is not a promising clinical alternative. Eye pressure does correlate with CSF pressure and various approaches have been used since eye pressure assessment is a common ophthalmological procedure.

Two types of intra ocular pressure measurement have been reported, with varying correlations to intra cranial pressure (ICP). These include non-contact air tonometry, which measures intra ocular pressure. This technique has produced conflicting results and at best provides only a rough estimate of ICP. The other reported technique is ophthalmodynometry, which is an aplanatic technique. This technique applies pressure to the cornea and measures the intra ocular arterial pulse wave. Pressure is applied to the corneal surface until the intra ocular arterial pulse wave (produced by the ophthalmic artery) is obliterated. The pressure at which this happens has been termed intra cranial arterial pressure and some have used this pressure to infer changes in ICP. However, this measure cannot be equated with ICP.

There have been previous attempts by other researchers to acoustically measure ICP in animals, but although they have proven the validity of the concept, they have not been practical for portable use in humans. Semmlow and Fisher ("A noninvasive approach to Intra cranial pressure monitoring", *Journal of Clinical Engineering*, 1982, vol. 7, pp. 73-78) observed in young dogs that the response of the head to low-level audible vibrations correlates with ICP elevation. Stevanovic et al. ("The effect of elevated Intra cranial pressure on the vibrational response of the bovine head", *Annals of Biomedical Engineering*, 1995, vol. 23, pp. 720-727) demonstrated the correlation of audible vibration with ICP in sheep, artificially elevating ICP and monitoring the acoustic signal. However, although their method did not require surgery within the skull cavity, it did require implantation of screws in the skull, making it impractical for a portable system.

There is a need for a technique that can be used to non-invasively monitor intra cranial pressure (ICP). There is a need for a portable, non-invasive sensor for measuring ICP in casualties with traumatic head injury, suitable for use in the battle area and during medical evacuation as well as in hospital conditions. This will allow monitoring to prevent secondary brain damage. Timely identification and treatment of elevated ICP will greatly improve the chances of survival of these patients.

SUMMARY OF THE INVENTION

It is therefore an object of the present invention to provide a non-invasive technique for detecting increases in brain pressure.

Another object of the invention is to provide a portable sensor for measuring ICP suitable for use at trauma sites as well as in hospital conditions.

A further object of the invention is to enable timely identification and treatment of elevated ICP.

The technique of the invention is to use acoustic signals and transducers on the surface of the skin of the head and over closed eyelids to non-invasively monitor intra cranial pressure. Intra cranial pressure changes are detected non-invasively using acoustic eye patches that are comfortable, accurate and provide a rapid and sensitive reading. A piezoelectric film sensor is placed in contact with the eye or eyelid of each eye.

A method and apparatus according to the invention measures intra cranial pressure by using an acoustic eye patch conformably adapted to an eyeball of a patient, the eye patch having sensors for measuring acoustic signals. The eye patches have piezoelectric film sensors for measuring the acoustic signal. An ultrasonic sweep generator applies acoustic signals across the skull of the patient, the signals sweeping a predetermined range. An analyzer determines from an output of the acoustic eye patch an intra cranial pressure. In one embodiment the predetermined range is in the ultrasonic band and an analyzer determines from the output of the sensors a resonant frequency and a damping of acoustic amplitude at the resonant frequency, there being a correlation between the damping and intra cranial pressure. In another embodiment the predetermined range includes a range less than 20 kHz and the analyzer determines retinal artery pulsations, with pressure being applied to the eye until the pulsations disappear, such pressure being a measure of intra cranial pressure.

BRIEF DESCRIPTION OF THE DRAWINGS

The foregoing and other objects, aspects and advantages will be better understood from the following detailed description of a preferred embodiment of the invention with reference to the drawings, in which:

FIG. 5 is a table of invasive measurements of ICP for five patients used for calibrating acoustical recordings made from the skull and eye.

FIG. 10 is a table showing differences in direct ICP measurements and acoustic intensity attenuation recorded at the eye for various patient pairs.

DETAILED DESCRIPTION OF A PREFERRED EMBODIMENT OF THE INVENTION

Figure 1:
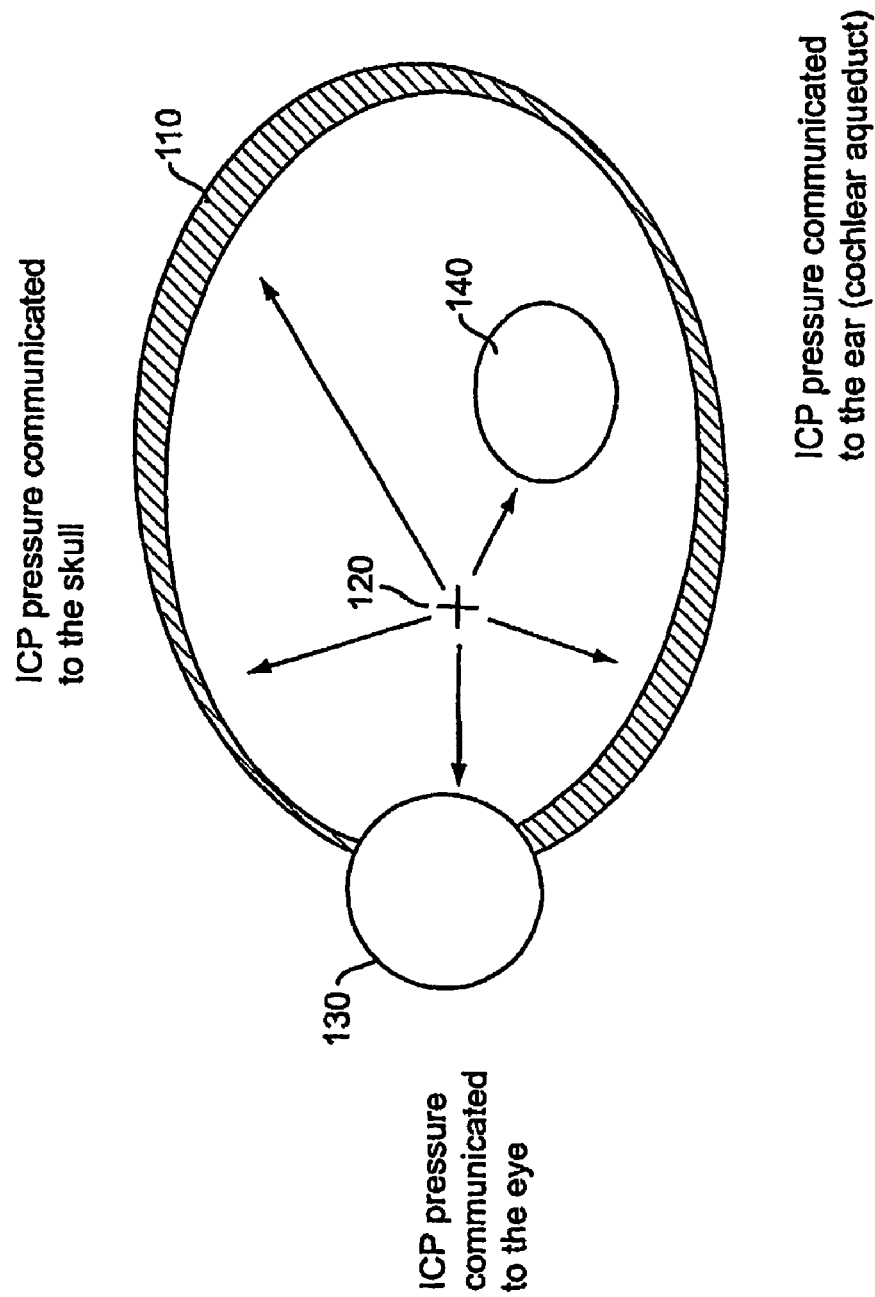
FIG. 1 is a conceptual schematic showing the effects of intra cranial pressure.

Referring now to the drawings, and more particularly to FIG. 1, there is shown a conceptual schematic of a skull 110, within which and upon which the brain's cerebral spinal fluid (CSF) exerts pressure 120. This pressure 120 is not only communicated to the skull 110 but is also communicated to the eye 130 and the ear 140. The brain and the skull are coupled resonant systems that will respond in a predictable fashion to pressure increases. Changes in acoustic damping are correlated with changes in cerebral spinal fluid (CSF) or intra cranial pressure (ICP).

Any physical or biological system that has an acoustic resonance will be characterize by a narrow range of frequencies which will cause the system to oscillate, i.e. force resonance. A fine wine glass can be forced into vibration and it will oscillate with the greatest amplitude at its resonance frequency. Sometime the amplitude is so great the glass shatters. However, natural resonance can be reduced in amplitude by damping. If the glass is filled with wine or a gel the amplitude of oscillation will be reduced. Furthermore, if the wine or gel is placed under pressure, further amplitude reduction will be observed.

The skull, brain and eye are all resonant structures. The skull's natural resonance is around 2 kHz. That is, if acoustic energy with a frequency of 2 kHz is applied across the skull, the intensity of the acoustic energy measured elsewhere on the skull will be high relative to such measurements taken at frequencies which are outside the range of natural resonance. With increased ICP there will be more pressure on the inside of the skull such that its natural resonant oscillations will be damped. The resonance of the brain is about 15 kHz and with increased ICP its oscillation too will be damped.

The brain's damped oscillation in response to forced vibration (e.g. sound applied to the head) will be communicated to the eyeball and can be recorded off the lid. Thus increased ICP increases damping of acoustic vibrations in the brain and skull, which will reduce the acoustic oscillation of these structures, and that reduced oscillation can be recorded on the eye. The amount of oscillation reduction is directly proportional to actual ICP.

Other frequencies than the resonant frequency can be used, but the effects of increased ICP will be more difficult to measure because at non-resonant frequencies the difference between natural oscillation and oscillation under damping will be very small, due to the frequency response of any resonant structure. The largest difference between the natural and damped frequencies is near the resonant frequency. However, the method of the invention does not use a specific frequency because there will be range of resonant frequencies in the human population due to individual geometries.

Figure 2A:
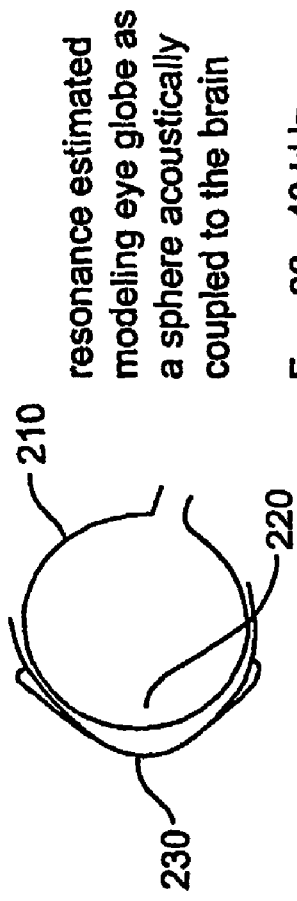
FIG. 2 is a diagram showing a piezoelectric film sensor in contact with the eye or eyelid.
Figure 2B:
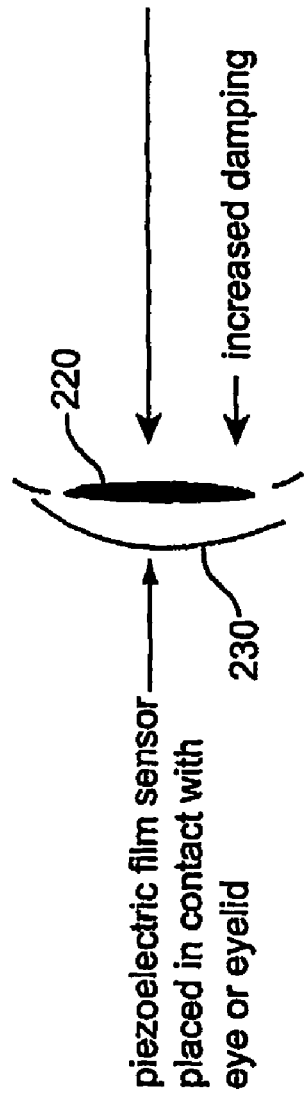

Turning now to FIG. 2, there is shown a diagram of the eye resonance pressure effect used by the present invention. The invention capitalizes on the acoustic resonant properties of the eye 210, a globe that can be modeled accurately as a sphere. Sixty percent of the globe is bounded by bone, representing a high impedance interface. Calculations of resonant frequencies range from approximately 30-50 kHz (e.g. a nominal calculation of 33-43 kHz, as shown). Ultrasonic resonance is expected, given the small radius of the eye (~0.75 cm). However, variations in anatomical features and departures from precisely spherical geometry make exact predictions difficult. Therefore, the method of the invention is to sweep tones from well below to well above projected resonant frequency. This is a prudent tactic to ensure that resonant frequencies will be covered.

As pressure is increased by the CSF of the brain on the globe of the eye 210, intra ocular pressure (IOP) rises. Increases in IOP will increase the acoustic damping. Increased acoustic damping will be reflected in a reduction in intensity of the signal communicated within the eye and to that portion 220 of the eye closest to the sensor 230 placed comfortably over the closed eyelid or the eye. The sensors 230 are constructed of piezoelectric film, coated with Mylar, and record the intensity of the signal damped by increases in IOP.

The eye pressure is an indicator of brain ICP. The pressure increase in the brain can be detected as a change in the sound propagation amplitude through the eye. Conversely increased eye pressure, in the context of normal brain ICP, will also be detected as a change in acoustic propagation through the eye. As the ICP or cerebral spinal fluid pressure (CSF) increases there is increased acoustic damping in the eye which will be reflected as a change in acoustic pressure. The sound waves are picked up by a piezoelectric film sensor placed in contact with the eye or eyelid. Furthermore, if the sensor is placed in the eye, a high frequency response can be consistently recorded. However, if the recording sensor touches the skull, the resulting spectrum looks much like that recorded from the skull. Consequently, it is important that the sensor not come into contact with the eye socket.

Figure 3:
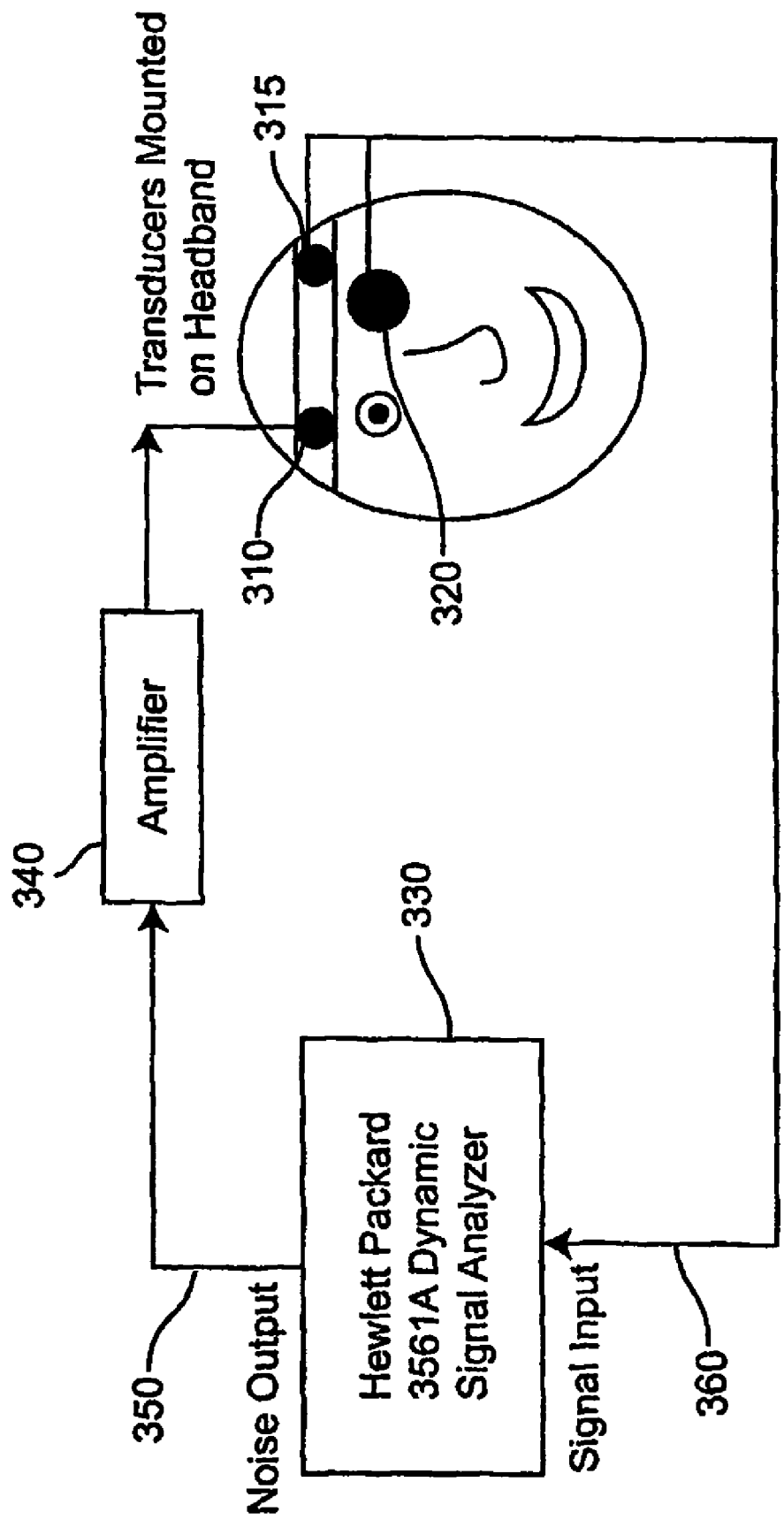
FIG. 3 is a diagram of an apparatus for acoustic stimulation of the brain.

FIG. 3 shows a monitoring apparatus for stimulating the brain with acoustic vibrations and recording from the eye or eyes and/or the skin of the head the resulting acoustic energy. The preferred location for a recording sensor for the head is over the forehead. Noise output 350 is fed to amplifier 340 and the amplified signals are applied to the brain via drivers 310 mounted on a headband, generally in front 310 and in back (not shown). The signals pass through the brain and are recorded at eye sensor 320 and/or a forehead sensor 315, the recordings then providing signal input 360 to signal analyzer 330.

Figure 4:
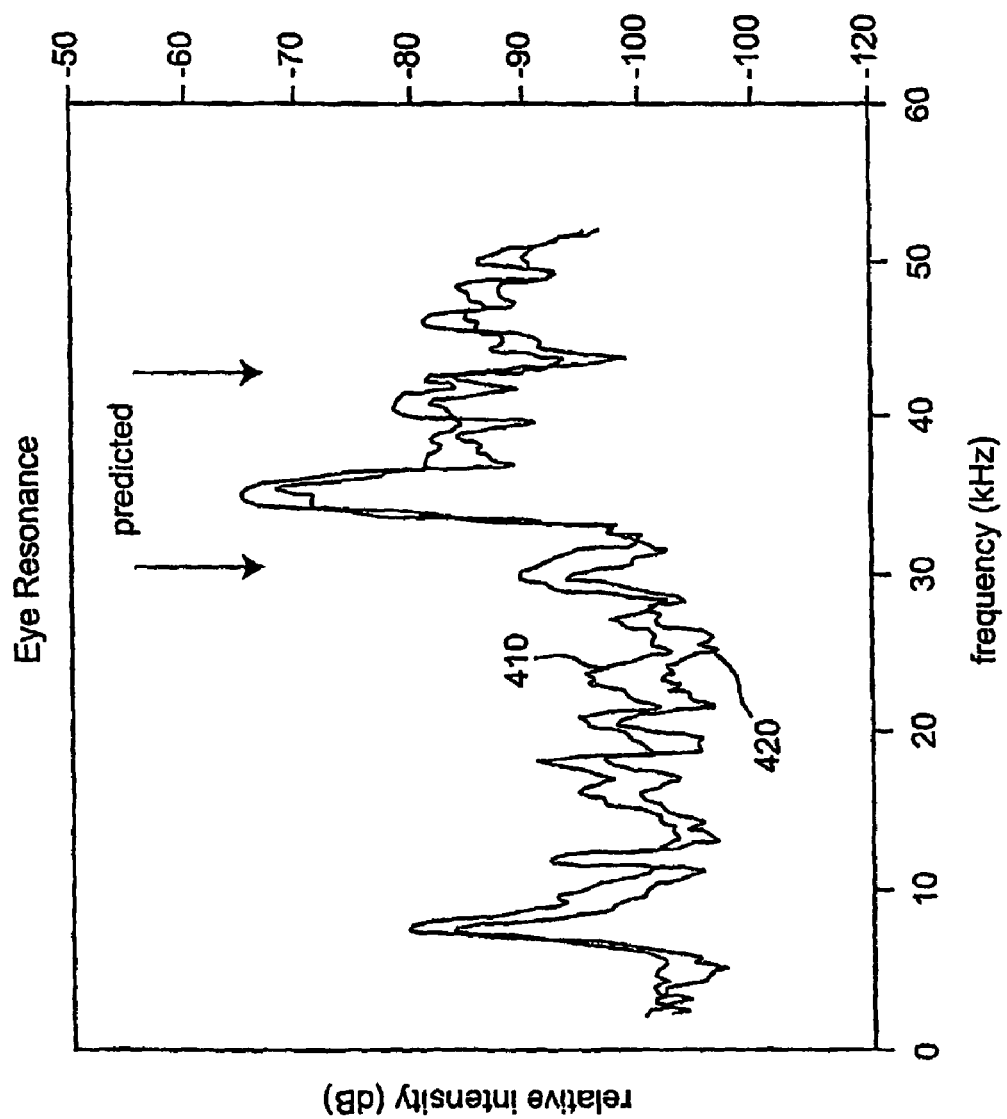
FIG. 4 is a graph showing the intensity of vibration across a range of frequencies recorded at the eye responsive to sound energy applied to the skull.

FIG. 4 shows a spectrum of vibration recorded from a closed eyelid in response to sound energy delivered to the skull. The acoustic energy was applied in a scan covering the range up to 50 kHz. The corresponding readings at the eye were attenuated in the range of –5 to –10 db. Modeling the eye as a sphere under some boundary condition would predict a resonance in the 30-50 kHz range. Actual recordings as shown in FIG. 4 indicate a range of 33-45 kHz for resonance. Clearly, the globe of the eye is not an exact sphere. The upper tracing 410 is under normal pressure and the lower tracing 420 is recorded during a valsalva maneuver, which elevated the ICP and dampened the recorded signal.

FIG. 5 is a table showing ICP measurements for five subjects who were implanted with a pressure sensor in the skull. The subjects are identified by their initials in the patient column 510. For each of these subjects, the invasive monitoring method (ventriculostomy) is shown in column 520. The measured ICP is shown in column 530. These measurements served as reference for the acoustical recordings made from the skull and eye. The ICP pressures ranged from 7-20 mm Hg. Pressures under 5 Hg are considered normal. Pressures over 10 mmHg are considered elevated and warranting clinical management.

It can be seen from FIG. 5 how calibration of the acoustic measurement is accomplished by reference to patient data where ICP is measured with a sensor placed directly in the brain (i.e. ventriculostomy as recorded in FIG. 5), and at the same time acoustic signals are measured at the eye as described above.

Figure 6:
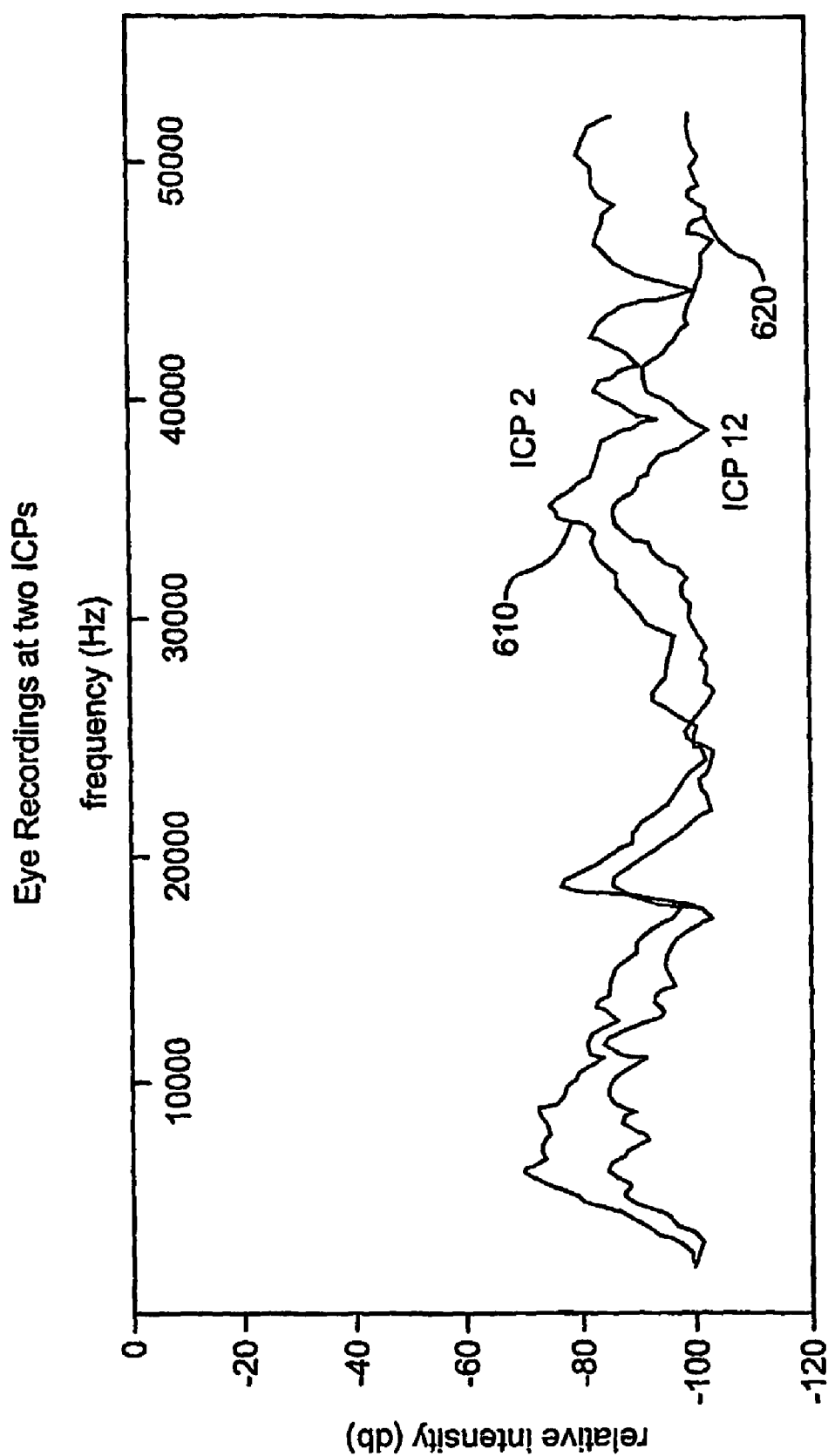
FIG. 6 is a graph showing acoustic intensity over a frequency range recorded at the eye for two patients with different ICP values.

FIG. 6 shows eye sensor recordings of relative acoustic intensity from two individuals, one 610 with normal ICP (2 Hg) and one 620 with slightly elevated ICP (12 Hg). Note the reduction in acoustic amplitude (i.e. further attenuation) with elevated ICP.

Figure 7:
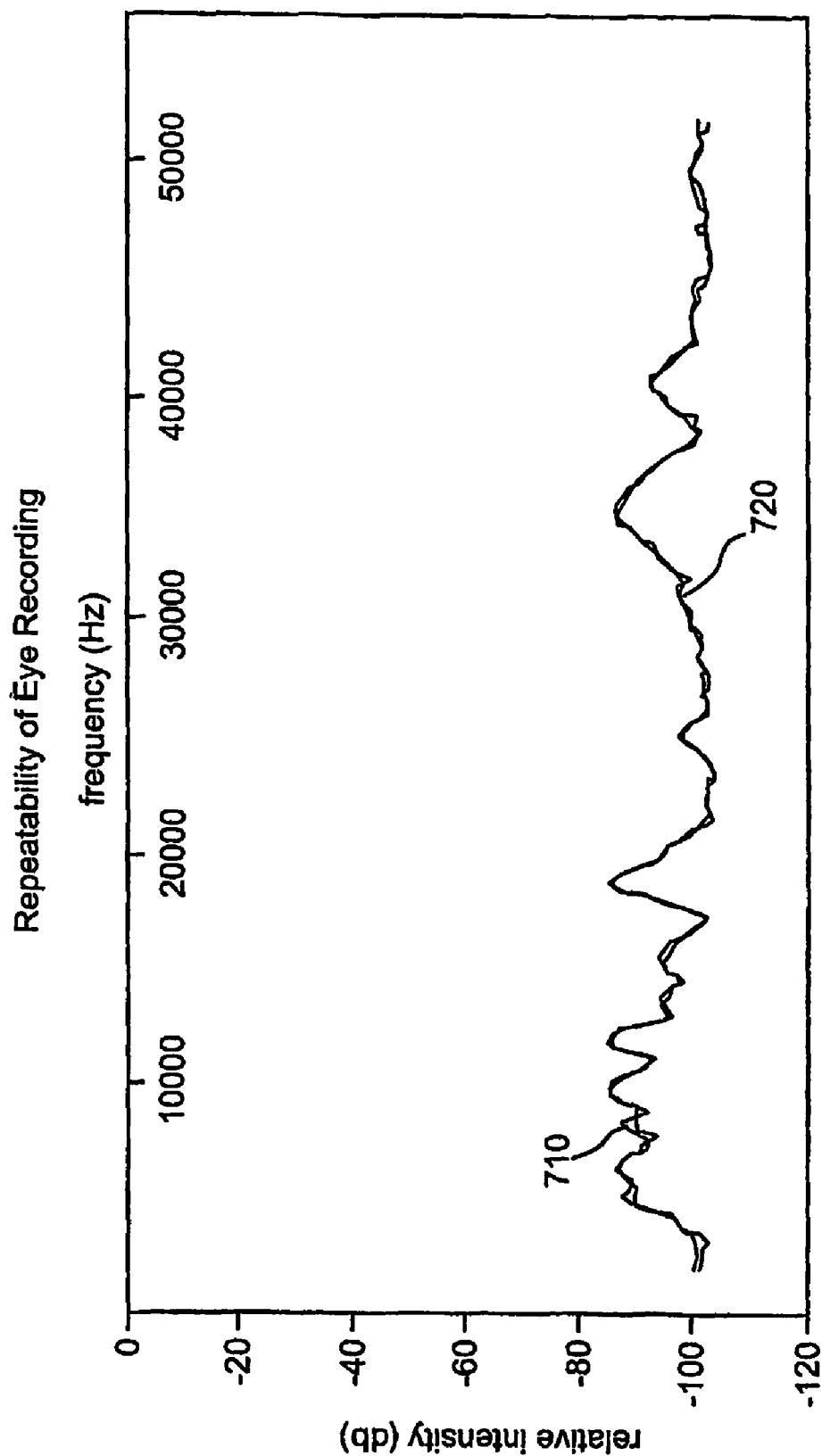
FIG. 7 is a graph showing the consistency of separate acoustic intensity recordings for the same patient.

FIG. 7 demonstrates the repeatability of the measurements taken using the technique of the invention. Measurements of the relative intensity of acoustic signals over a frequency range up to 50 kHz received at an eye sensor were taken from the same subject on two separate occasions. Trace 710 shows the results on one occasion and trace 720 shows the results on a second occasion. It will be observed that the two traces provide results that are very close, making it difficult to distinguish the traces shown on FIG. 7.

Figure 8:
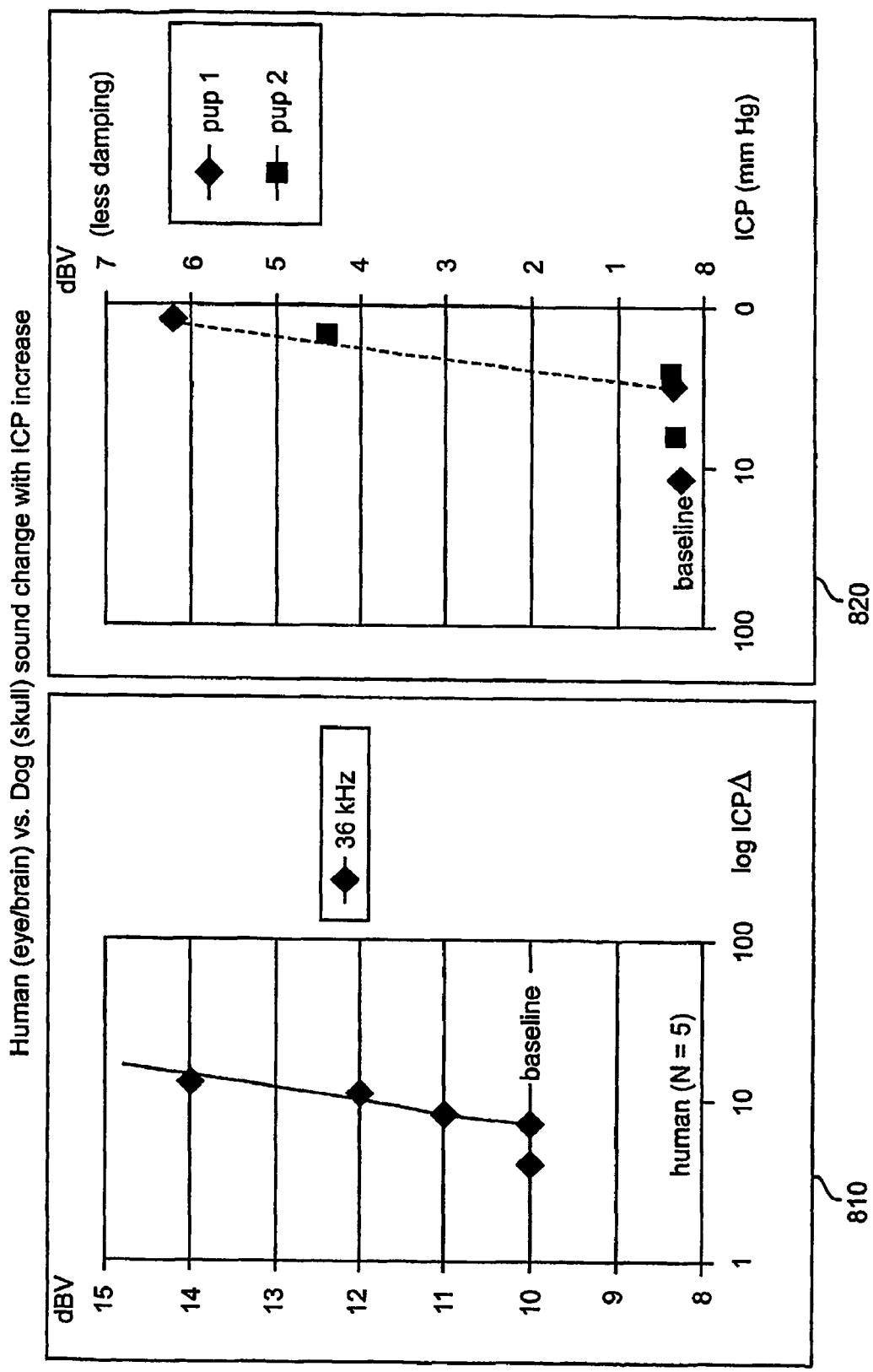
FIG. 8 compares graphs showing a linear relationship between ICP and damping of acoustic intensity at a resonance frequency in humans and dogs.

The left panel 810 of FIG. 8 shows that there is a linear relationship between ICP (the logarithmic horizontal scale, in ICP delta over normal, i.e. the difference between the measured ICP and a normal ICP) and eye recordings of sound amplitude (relative attenuation, in db volts, on the vertical scale) in human subjects. In this particular example 36 kHz was chosen as the resonant frequency because it had the best signal to noise ratio in the recording, and data for five human subjects is shown. A linear relation between ICP pressure and skull vibration is also suggested in the dog model shown in the right panel 820, using data taken from Semmlow and Fisher. While Semmlow and Fisher used skull sensors and did not use, or indicate an understanding of the significance of, resonant frequencies the linear relationship between increased cranial pressure and damping of acoustic signals is nonetheless demonstrated. Increased sound attenuation was arbitrarily defined as damping. Damping reduces sound transmission as indicated in the eye recordings in humans as well.

Figure 9:
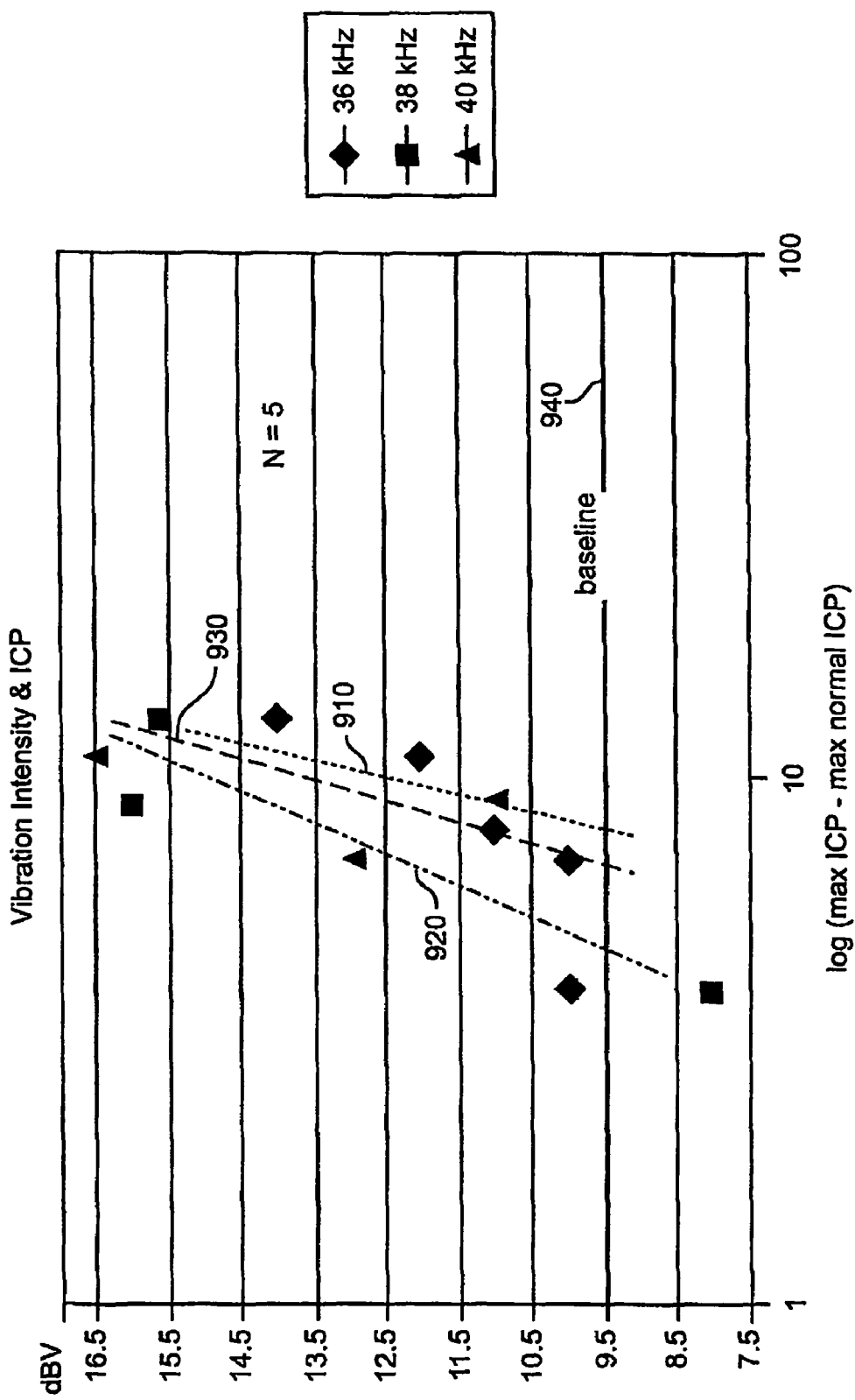
FIG. 9 is a graph showing a linear relationship between ICP and damping of acoustic intensity at several frequencies in the resonance range.

FIG. 9 shows that other frequencies (in the resonance range) can also be used to predict ICP based on a linear function. As with the first panel 810 of FIG. 8, the ICP delta over normal is shown logarithmically along the horizontal scale and relative attenuation of the acoustic signal is shown on the vertical scale. Data is plotted for frequencies of 36 kHz (whose results are summarized by plot line 910), 38 kHz (whose results are summarized by plot line 920) and 40 kHz (whose results are summarized by plot line 930). Likely frequencies higher or lower than this range can also be used. It should be noted that the differences in degree of resonance within the resonant frequency range are not in the form of a smooth bell curve. This may be seen from the shape of the graph within the predicted range shown on FIG. 4. Thus the linearity comparisons shown in FIG. 9 between data for 36 kHz, 38 kHz and 40 kHz (as shown by comparing lines 910, 920 and 930, respectively) may not be in the same order as the resonant frequencies themselves.

The baseline 940 in FIG. 9 represents a nominal value that serves as a practical dividing line between cases needing clinical attention and those where clinical attention may not be called for. In practical operation, the invention will be used by medical personnel at a trauma site. The analyzer of the invention may be implemented by an algorithm that automatically identifies a resonant frequency from an acoustical scan and uses calibration data (as described in connection with FIG. 5) to correlate signal damping at the resonant frequency with an equivalent ICP. The algorithm then provides at several levels the results of the acoustic readings translated into an equivalent cranial pressure. Below a certain level (e.g. 2 mm Hg), the readout of the analyzer would simply indicate that cranial pressure is not a concern. Above that level but below a baseline level, the readout would indicate that the patient's cranial pressure condition is not clear, but is not necessarily of concern. A medical technician using the invention may or may not continue to monitor the patient.

However, above the baseline, the readout of the analyzer would show the numerical value of the equivalent cranial pressure. The clinical concern is whether the pressure is increasing. After a delay, the length of which would be based upon the experience and judgment of the medical technician using the invention, another reading would be taken. If the reading showed an increase in intra cranial pressure, medical attention would be indicated. In general, variability between human subjects and variability in the circumstances make it difficult to say whether a particular ICP reading is elevated or not. The research underlying the invention and disclosed herein shows, however, that there is enough commonality across a range of human subjects and enough repeatability in the invention's measures of ICP that the invention can be of practical utility in a clinical setting.

FIG. 10 shows differences in direct ICP measurements and intensity attenuation recorded on the eye as seen for various combinations of patients over the range of 7-20 Hg in five subjects, the same five subjects shown in FIG. 5 and used in FIG. 9. These acoustical difference data were significant at the p=0.0001 level. The data in FIG. 10 demonstrates that the correlation between ICP and the measurement of acoustic attenuation in accordance with the invention is useful across a range of human subjects. Even when the results from different subjects are compared (here shown by measured ICP), the comparative measures of acoustic attenuation (here shown in a delta of dB volts) are consistent.

It should be noted that there are low frequency oscillations of the eye that are a reflection of cardiovascular support. If the eye sensor 240 is placed on the eye these low frequency oscillations (<20 Hz) can be recorded. If pressure is placed on the globe 210 (e.g. by simply pressing the sensor patch in toward the eye) there will be a point that the globe pressure is equal to the ICP. This can be detected by the eye sensors. Thus the method of the invention can be used to detect retinal artery pulsations using the piezoelectric film sensor 230 on the eye, and then to determine ICP by applying pressure on the eye until pulsations disappear.

Additional value using this technique to measure ICP may lie in its use in conjunction with trans-cranial acoustical measurement. In this manner, changes in an acoustical signal generated at the eye may be measured trans-cranially, or trans-cranially produced acoustical signals could be measured at the eye as described above. Thus as ICP changes the acoustical signals generated across these points will be changed. Furthermore, the ability to bilaterally measure the signals using both eyes may assist in confirming measures. Alternatively, the potential may exist to allow detection of hemispheric location of large accumulations of intra-cranial blood after trauma, such as epidural and subdural hematomas.

A non-invasive monitor is an important advance in emergency room medicine, for immediate use before implantation of invasive sensors. The present invention is a notable improvement over the few previous acoustic devices for assessing intra cranial pressure because it is simple, does not require extensive computing power, and is reliable from trial to trial. If the brain is stimulated at or near its resonant frequency the amplitude recorded from external sensors will reflect damping produced by increases in pressure. The acoustic features of fluid pressure increases are stable.

While the invention has been described in terms of preferred embodiments, those skilled in the art will recognize that the invention can be practiced with modification within the spirit and scope of the appended claims.

Having thus described our invention, what we claim as new and desire to secure by Letters Patent is as follows:

1. An apparatus for measuring intra cranial pressure, comprising:
    an acoustic eye patch conformably adapted to an eyeball of a patient, said eye patch having sensors for measuring acoustic signals in the brain, without the sensors coming into contact with the skull;
    a sweep generator for applying acoustic signals to the brain across the skull of the patient, said signals sweeping a predetermined range, a resonant frequency of said eyeball of the patient being within said predetermined range, said predetermined range covering a corresponding range of resonant frequencies across a range of patients; and
    an analyzer for determining an intra cranial pressure from a degree of damping of said swept acoustic signal at the resonant frequency of said eyeball of the patient, said intra cranial pressure being transmitted directly to said eyeball where said pressure and said damping are measured without attenuation by the skull of the patient, said resonant frequency and degree of damping being determined from an output of the acoustic eye patch, wherein said degree of damping is correlated to a measure of said intra cranial pressure.

2. The apparatus of claim 1, wherein said predetermined range is an ultrasonic resonance range.

3. The apparatus of claim 1, wherein the acoustic eye patch is adapted to be applied to both eyeballs of the patient.

4. The apparatus of claim 2, wherein the predetermined resonance range is 30-50 kHz.

5. The apparatus of claim 1, wherein the acoustic eye patch sensor is a piezoelectric film.

6. The apparatus of claim 3, wherein the analyzer determines coherence between eyeballs of the patient.

7. The apparatus of claim 1, wherein said analyzer detects retinal artery pulsations, and wherein pressure is applied to the eye via said acoustic eye patch until the retinal artery pulsations disappear, said applied pressure being a further measure of intra cranial pressure.

8. A method for determining intra cranial pressure, comprising the steps of:
    conformably adapting an acoustic eye patch to an eyeball of a patient, said eye patch having sensors for measuring acoustic signals in the brain, without the sensors coming into contact with the skull;
    applying acoustic signals to the brain across the skull of the patient, said signals sweeping a predetermined range, a resonant frequency of said eyeball of the patient being within said predetermined range, said predetermined range covering a corresponding range of resonant frequencies across a range of patients; and
    determining an intra cranial pressure from a degree of damping of said swept acoustic signal at the resonant frequency of said eyeball of the patient, said intra cranial pressure being transmitted directly to said eyeball where said pressure and said damping are measured without attenuation by the skull of the patient, said resonant frequency and degree of damping being determined from an output of the acoustic eye patch, wherein said degree of damping is correlated to a measure of said intra cranial pressure.

9. The method of claim 8, wherein said predetermined range is an ultrasonic resonance range.

10. The method of claim 8, wherein the acoustic eye patch is applied to both eyeballs of the patient.

11. The method of claim 9, wherein the predetermined resonance range is 30-50 kHz.

12. The method of claim 8, wherein the acoustic eye patch sensor is a piezoelectric film.

13. The method of claim 10, wherein the analyzer determines coherence between eyeballs of the patient.

14. The method of claim 8, wherein said analyzer detects retinal artery pulsations, and wherein pressure is applied to the eye via said acoustic eye patch until the retinal artery pulsations disappear, said applied pressure being a further measure of intra cranial pressure.

* * * * *